United States Patent
Xie et al.

(10) Patent No.: US 11,179,330 B2
(45) Date of Patent: Nov. 23, 2021

(54) DOXEPIN ORAL TRANSMUCOSAL FILM

(71) Applicant: Xiamen LP Pharmaceutical Co., Ltd., Xiamen (CN)

(72) Inventors: Liyan Xie, Xiamen (CN); Yuantao Song, Xiamen (CN); Shengkai Cao, Xiamen (CN); Zhoue Gao, Xiamen (CN); Rongbin Ling, Xiamen (CN)

(73) Assignee: Xiamen LP Pharmaceutical Co., Ltd., Fujian (CN)

( * ) Notice: Subject to any disclaimer, the term of this patent is extended or adjusted under 35 U.S.C. 154(b) by 76 days.

(21) Appl. No.: 16/746,528

(22) Filed: Jan. 17, 2020

(65) Prior Publication Data
US 2021/0186859 A1   Jun. 24, 2021

(30) Foreign Application Priority Data

Dec. 23, 2019 (CN) .......................... 201911338203.0

(51) Int. Cl.
| | |
|---|---|
| *A61K 9/00* | (2006.01) |
| *A61K 31/335* | (2006.01) |
| *A61K 47/10* | (2017.01) |
| *A61K 47/22* | (2006.01) |
| *A61K 47/32* | (2006.01) |
| *A61K 47/38* | (2006.01) |
| *A61K 47/26* | (2006.01) |

(52) U.S. Cl.
CPC ............ *A61K 9/006* (2013.01); *A61K 31/335* (2013.01); *A61K 47/10* (2013.01); *A61K 47/22* (2013.01); *A61K 47/26* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 2003/0068378 A1* | 4/2003 | Chen ................... | A61K 31/505 424/486 |
| 2007/0207192 A1* | 9/2007 | Holl ..................... | A61K 9/006 424/449 |
| 2011/0318412 A1 | 12/2011 | Schioppi et al. | |

OTHER PUBLICATIONS

H. Castán, et al., "Design, development and characterization of buccal bioadhesive films of Doxepin for treatment of odontalgia". Drug Delivery, 2015; 22(6): 869-876.

* cited by examiner

*Primary Examiner* — Melissa S Mercier
(74) *Attorney, Agent, or Firm* — Perkins Coie LLP; Viola T. Kung

(57) ABSTRACT

The present invention provides an oral transmucosal film or patch for delivering doxepin through the buccal mucosa or sublingual mucosa. The film or patch is a bilayer structure containing a mucoadhesive layer with amorphous doxepin and soluble backing layer without doxepin. The film or patch has satisfactory bioavailability and improved palatability. The mucoadhesive layer comprises 0.5-25% (w/w) of doxepin, 50-96% of one or more film-forming agents, 1-30% (w/w) of one or more adhesives, and 0.05-5% (w/v) of one or more stabilizers. The backing layer comprises 80-100% (w/w) of one or more film-forming agents. Preferred adhesives include povidone, carbomer, and polycarbophil. Preferred stabilizers include butylated hydroxyanisole (BHA), butylated hydroxytoluene (BHT), citric acid, and ascorbic acid.

9 Claims, No Drawings

DOXEPIN ORAL TRANSMUCOSAL FILM

This application claims the priority of Chinese Application No. 201911338203.0, filed Dec. 23, 2019; which is incorporated herein by reference in its entirety.

FIELD OF INVENTION

The present invention relates to an oral transmucosal film for delivering doxepin through the buccal mucosa or sublingual mucosa.

BACKGROUND OF THE INVENTION

According to the research of World Health Organization, one third of the population worldwide has insomnia or sleep disorder. The research of the Chinese Medical Association reports that the prevalence rate of sleep disorder in China reaches to 42.7%, and about 300 million of the middle-aged group have sleep disorders. Moreover, according to the Chinese Sleep White Paper 2016, the sleep disorder population in China was about 310 million, which is about 22.5% of the total population.

Currently, three kinds of drugs are clinically used to treat insomnia, including barbiturates (the first generation), benzodiazepines (the second generation), and non-benzodiazepines (the third generation). However, these drugs affect directly on the central nervous system to make treated subjects excited or inhibited, and the treated subjects have addiction potential as well as overdose potential. Therefore, these drugs are classified as Class II psychotropic drugs. In recent years, research on new hypnotic drugs has been strengthened, making hypnotic drugs gradually move toward "idealized sleep" (improving sleep time and quality, having no effect on mental, motor function and memory, no dependence and rebound insomnia). New hypnotics such as Dorset, Ramelteon, and Agomelatine have emerged.

Doxepin is a histamine H1-receptor antagonist with high affinity for H1-receptors. Doxepin produces sleep-promoting effects through the histamine system. This mechanism is different from any other approved prescription hypnotics. Doxepin hydrochloride promotes patients to sleep and maintain the sleep for 7-8 hours. It has no overdose potential and therefore is not listed as controlled substance. Moreover, no side effects, such as withdrawal effects or other physical dependence side effects, were observed or indicated during clinical research development.

Doxepin tablets were developed by Pernix Therapeutics Holdings, Inc. and approved by FDA in March 2010. Doxepin is well-absorbed from the gastrointestinal tract but between 55 and 87% undergoes first-pass metabolism in the liver, resulting in a mean oral bioavailability of only about 13-45%. In addition, because doxepin tablets have a slow onset, patients need to take doxepin tablets in advance (about 30 minutes) of bedtime. Doxepin tables have a relatively long time ($T_{max}$ 3.5 h) to reach the peak plasma concentration. Further, the oral tablet administration is affected by food. Patients are required to fast three hours before or after taking doxepin tablets, which is inconvenient and causes incompliance of patients.

There exists a need for a method and a composition for delivering doxepin with improved bioavailability, rapid effect and high convenience.

DETAILED DESCRIPTION OF THE INVENTION

The inventors have discovered a pharmaceutical composition suitable for buccal or sublingual administration of doxepin with improved bioavailability. In one embodiment, the pharmaceutical composition is in an oral film or patch format. The doxepin oral transmucosal film or patch of the present invention is essentially uniform in thickness and color, without bubbles, and with good stability under common storage conditions. The buccal transmucosal film of the present invention quickly adheres to the buccal mucosa, promotes drug absorption, and has high bioavailability. The pharmaceutical composition of the present invention makes it possible to administer doxepin buccally or sublingually by a transmembrane route. Buccal epithelium is a relatively permeable non-keratinized tissue; where blood vessels drain directly into the jugular vein.

The pharmaceutical composition provides a good water solubility and typically is dissolved in water completely in less than 5 minutes. The pharmaceutical composition of the present invention is designed to achieve a desired doxepin absorption profile and peak blood level and to provide a favorable pharmacokinetic profile with a good bioavailability.

The present invention provides a doxepin oral transmucosal film or patch, which is useful for treating insomnia characterized by difficulty with sleep maintenance. The film or patch is easy to use with a rapid onset of action to significantly reduce sleep onset latency and to achieve fast falling asleep. It is advantageous that the drug is absorbed through the oral mucosa, which avoids gastrointestinal degradation and liver first pass effect, and consequently the bioavailability of doxepin is improved dramatically.

In order to avoid the first pass effect when orally administering doxepin, the inventors have discovered a pharmaceutical composition suitable for buccal or sublingual delivery of doxepin with improved bioavailability as much as 4 to 8 times of the doxepin tablets. The doxepin oral transmucosal film or patch of the present invention is essentially uniform in thickness and color, and without bubbles.

The active ingredient doxepin in the present oral transmucosal film is in an amorphous form to increase the dissolution rate in buccal or sublingual administration. The amorphous doxepin is rapidly released and absorbed, which provides a fast onset of action after administered. With added stabilizer in the film, the amorphous doxepin maintains a good stability under common storage conditions.

The oral transmucosal film of the present invention quickly adheres to the buccal or sublingual mucosa and is absorbed directly into the blood vessels via buccal or sublingual mucosa, which avoids gastrointestinal degradation and bypasses the liver first pass effect. The buccal transmucosal film of the present invention promotes the absorption of doxepin, and provides a high bioavailability of doxepin.

Doxepin can cause numbness in the tongue and throat, which results in a feeling of discomfort in mouth when administered orally. The oral transmucosal film of the present invention is in a bilayer film having a mucoadhesive layer comprising doxepin, and a backing layer that is drug free. The backing layer effectively prevents the drug in the mucoadhesive layer from diffusing to the oral cavity during oral administration and thus preventing a patient from feeling numbness in the tongue and throat and improving the compliance of a patient.

The oral transmucosal film of the present invention is administered buccally or sublingually by placing the pharmaceutical composition in the mouth of a subject, either under the tongue (sublingual) or between the gum and the cheek (buccal). Doxepin is absorbed through the mucous membranes of the mouth to enter the bloodstream, which reduces the time to reach a peak plasma concentration ($T_{max}$ about 0.5-1.5 hours), comparing to that of doxepin tablets ($T_{max}$ about 3.5 hours). Additionally, doxepin in the present invention enters bloodstream through absorption so the administration is not affected by food.

The pharmaceutical composition is preferably in a film form, in a weight of about 10-200 mg, preferably about 10-100 mg or 20-100 mg.

The oral transmucosal doxepin film of the present invention is in a bilayer film form comprising a mucoadhesive layer and a backing layer. The mucoadhesive layer contains about 0.5-25% w/w of doxepin or a pharmaceutically acceptable salt thereof in an amorphous form, about 50-96% w/w of a first film-forming material, about 1-30% w/w of an adhesive, and about 0.05-5% w/w of a stabilizer.

"Pharmaceutically acceptable salts," as used herein, are salts that retain the desired biological activity of the parent compound and do not impart undesired toxicological effects. The backing layer is water-soluble and comprises 80-100% w/w of a second film-forming material to prevent doxepin from diffusing to the oral cavity of a patient during oral administration.

"About" when used in this application, refers to ±10% of the recited value.

Unless otherwise specified, % used in this application refers to weight by weight %.

The active ingredient in the pharmaceutical composition is doxepin or a pharmaceutically acceptable salt thereof, e.g., doxepin hydrochloride. The amount of doxepin in the present oral transmucosal film in general is 0.1-25 mg. The weight percentage of doxepin in the film in general is 0.01-50% w/w, preferably 0.5-25% w/w.

Film-forming materials useful in the mucoadhesive layer include one or more materials as follow: polyvinyl alcohol (PVA), hypromellose (HPMC), hydroxypropyl cellulose (HPC), copovidone, povidone, ethylene glycol and vinyl alcohol graft copolymer, xanthan gum, pectin, polyethylene oxide (PEO), and chitosan. Preferred film-forming materials include low viscosity materials such as hydroxypropyl cellulose (HPC), polyvinyl alcohol (PVA), hypromellose (HPMC), copovidone, ethylene glycol and vinyl alcohol graft copolymer (PVA-PEG). The viscosity of HPC is from about 100 to 600 mPa·s (millipascal·second) at 10% w/w concentration. The viscosity of HPMC is about 3-100 mPa·s at 2% w/w concentration. The weight percentage of film-forming materials in the film is in general about 50-96% w/w, or 60-96% w/w. The film-forming materials are compatible to doxepin and provide a suitable drug loading capacity, and are able to maintain doxepin at an amorphous state in the film. The mucoadhesive film formed is flexible and not brittle.

Film-forming materials useful in the backing layer include one or more materials as follows: polyvinyl alcohol (PVA), hypromellose (HPMC), copovidone, ethyl cellulose (EC), polyethylene oxide (PEO), and hydroxyethyl cellulose (HEC); these materials prevent the diffusion of doxepin from a mucoadhesive layer to the oral cavity during administration to improve palatability. On the contrary, povidone and PVA-PEG have negligible effects on improving the palatability of the oral film. The amount of film-forming materials is about 50-100% (w/w), or 80-100%. The backing film formed has a good flexibility.

Bioavailability is affected by the rate of doxepin absorbed through the oral mucosa and the time of the film adhering to the oral mucosa. The adhesives in the mucoadhesive layer enable the film to adhere to the mucosa until it is completely dissolved. In order to improve the drug bioavailability, the inventors screened a variety of adhesive agents. The inventors have discovered that different adhesive agents have different effects on the bioavailability of doxepin. Some adhesive agents such as carboxymethylcellulose sodium and sodium alginate, did not improve adhesiveness, and may suppress doxepin dissolution and reduce doxepin bioavailability. Some adhesives such as sodium carboxymethylcellulose and sodium alginate do not improve adhesiveness of the film. Adhesives suitable for the present invention include one or more materials as follows: povidone, polyglutamic acid, polycarbophil, carbomer, dextran sulfate, and chondroitin sulfate. Polycarbophil, carbomer and povidone are preferred adhesives. The suitable weight percentage of the adhesives in mucoadhesive layer is from about 1% to 30% w/w, and preferably 1-20% w/w. When the adhesives exceed 50% w/w, the amount of doxepin released from the film is decreased, and thus the bioavailability is lowered. The selected adhesives provide a good adhesion, and they have no impact on doxepin dissolution.

During the manufacturing process, doxepin is prepared in a solution and then the solution is coated on a substrate and dried into a film. Doxepin is in an amorphous form in the mucoadhesive layer so that the film can produce a fast dissolution rate and improve the bioavailability of doxepin. To improve the chemical stability of doxepin at an amorphous state in the film, one or more stabilizers are added in the formulation. The inventors have selected suitable stabilizers such ascorbic acid, citric acid, sodium citrate, butylated hydroxyanisole (BHA), and butylated hydroxytoluene (BHT), vitamin E. Preferable stabilizers include ascorbic acid, citric acid, BHA and BHT. The weight percentage of the stabilizer is from about 0.01% to 10% w/w, and preferably 0.05-5% w/w. Other stabilizers such as edetate disodium, sodium sulfite, sodium metabisulfite, and sodium bisulfite do not improve the stability of doxepin in an amorphous form.

Due to the bitter taste of doxepin, both layers of the film optionally contain a flavoring or taste masking agent to decrease its bitterness and increase patient compliance. The flavoring agent may include one or more ingredients as follows: sucrose, glucose, sodium saccharin, fructose, xylitol, stevia, aspartame, sucralose, neotame and acesulfame potassium, peppermint oil, menthol, orange flavor, pineapple flavor, cherry flavor, apple flavor, banana flavor, blueberry flavor, peach flavor, mango flavor, or grape flavor. Sucralose and menthol are preferred flavoring agents for the present invention. The amount of a flavoring agent in the composition is about 0.01-5%, preferably about 0.05-2% (w/w) in the mucoadhesive layer, and 0-5% w/w in the backing layer.

The coloring agent, which can be selected from the group consisting of FD & C colors, D & C colors, and combinations thereof, may be added into one or both layers of the film.

The oral transmucosal film of the present invention has the following advantages. Doxepin is completely dissolved and absorbed via the oral mucosa so that it has a fast onset of action and helps the patient fall into sleep quickly. Food intake has no effect on the oral transmucosal film, so patients have more flexibility in taking the drug. Furthermore, the present oral transmucosal film can improve bioavailability by 3 to 15 times compared to doxepin tablets. Therefore, the drug dosage can be reduced while maintaining the same pharmaceutical efficacy, which diminishes the side effect of the drug.

The present invention also provides a method for preparing doxepin oral transmucosal bilayer film. The method comprises the following steps: (a) mixing doxepin, the first film-forming material, the adhesive, and the stabilizer in a first aqueous solvent to prepare a mucoadhesive film solution; (b) coating the mucoadhesive film solution on a substrate and drying the film solution to form the mucoadhesive layer; (c) mixing a second film-forming material in a second aqueous solvent to prepare a backing film solution; (d) coating the backing film solution on the mucoadhesive layer and drying the backing film solution to form a bilayer film on the substrate, and (e) removing the bilayer film from the substrate to form the oral transmucosal doxepin film.

In step (a) and (c), an appropriate aqueous solvent comprises purified water and optionally organic solvent, such as ethanol, isopropanol, acetone, ethyl acetate, tert-butanol, dichloromethane, or a mixture thereof, from 0-75% w/w. Preferable organic solvents include ethanol or isopropanol. The aqueous solvents allow all the materials to dissolve completely and form a homogeneous solution. Using a higher concentration of an organic solvent such as 95% ethanol during preparation of the film keeps doxepin in a crystalline form and lowers the dissolution rate of doxepin.

In steps (a) and (c), a flavoring agent and a coloring agent is optionally added in the solution to improve the flavor and color.

In step (b) and (d), the drying temperature is about 40°-100° C., preferably about 50-80° C.

The substrate that the bilayer film formed on includes polyethylene terephthalate, polypropylene resins, and polymethylpentene resins.

After step (e), the bilayer film is optionally cut into a suitable size and shape, and then further wrapped or packaged.

The doxepin oral transmucosal film or patch of the present invention has a length of about 1-4 cm, and a width about 1-4 cm; preferably a length of about 1-3 cm, and width about 1-3 cm.

The present invention also provides a method for administering doxepin to a subject. The method comprises identifying a subject in need thereof, and administering to the buccal mucosa or sublingual mucosa of the subject the transmucosal film of the present invention.

The present film is useful in treating a subject that is a mammal, such as humans, horses, dogs, and cats. The present invention is particularly useful in treating humans.

The following examples further illustrate the present invention. These examples are intended merely to be illustrative of the present invention and are not to be construed as being limiting.

EXAMPLES

Example 1: Doxepin Hydrochloride Transmucosal Film (Crystalline State)

In this example, the doxepin hydrochloride was manufactured as a film dosage form, which can be administered buccally or sublingually. The formulation of this example is shown below.

| | |
|---|---|
| Doxepin hydrochloride (crystalline) | 3.0 mg (15% w/w) |
| Hypromellose | 16.88 mg (84.4% w/w) |
| FD&C Yellow No. 6 | 0.02 mg (0.1% w/w) |
| Sucralose | 0.1 mg (0.5% w/w) |
| 95% Alcohol | 105 mg (Removed during manufacturing process) |

Preparation: Dissolved/dispersed the doxepin hydrochloride into the solvent according to the formulation, then added the other components in the formulation, and stirred until they were completely dissolved. Set aside or vacuumed to remove air bubbles. Evenly coated the defoamed film solution on the conveyor belt and dried up at the temperature of about 50° C. to 80° C. The aqueous solvent was evaporated after drying. After the film was formed, cut the film into a suitable size and shape and packaged.

The doxepin hydrochloride transmucosal film prepared by the above method presented satisfactory film-forming performance and could be easily peeled off from the film base. Also, the films had a smooth appearance and uniform color. Moreover, the active ingredient doxepin hydrochloride crystal powder is dispersed evenly in the film. The x-ray powder diffraction shows that the doxepin hydrochloride was in a crystallized state in the film.

In the dissolution test, the drug powder was released and dissolved after the oral film was dissolved, and the dissolution rate was relatively slow (63% at 5 min).

TABLE 1

Dissolution Test Result (Crystalline Doxepin)

| | Media pH 6.8 Phosphate Buffer | | | |
|---|---|---|---|---|
| Time (min) | 5 | 10 | 20 | 30 |
| Dissolved (%) | 63 | 88 | 96 | 99 |

Various concentrations (80-95%) of alcohol and other solvents (isopropanol, ethyl acetate, and acetone) were also tried, and the doxepin hydrochloride in the produced transmucosal film was all in crystallized state and dispersed in the film as spots. Those transmucosal films had a slow dissolution profile as well.

Example 2: Doxepin Hydrochloride Transmucosal Film (Amorphous State)

In this example, the doxepin hydrochloride transmucosal film was prepared based on the method stated in Example 1. The formulation was modified to use purified water instead of 95% alcohol. The API of doxepin hydrochloride used in the formulation was in a crystalline state, and after the film was formed by the method in Example 2, the doxepin hydrochloride was converted into an amorphous state in the film.

| | |
|---|---|
| Doxepin hydrochloride (crystalline) | 3.0 mg (15% w/w) |
| Hypromellose | 16.88 mg (84.4% w/w) |
| FD&C Yellow No. 6 | 0.02 mg (0.1% w/w) |
| Sucralose | 0.1 mg (0.5% w/w) |
| Purified Water | 105 mg (Removed during manufacturing process) |

The doxepin hydrochloride transmucosal film prepared by this example had a smooth appearance and uniform color, without any noticeable crystal solid in the film. Meanwhile, the dissolution test showed that the drug substance was dissolved after the film was dissolved, and 98% was dissolved in 5 min. Thus, in terms of active substance dispersion uniformity in the film and dissolution rate, the amorphous doxepin hydrochloride transmucosal film prepared in this example is superior to the crystallized transmucosal film in Example 1.

TABLE 2

Dissolution Test Result (Amorphous Doxepin)

| | Media pH 6.8 Phosphate Buffer | | | |
|---|---|---|---|---|
| Time (min) | 5 | 10 | 20 | 30 |
| Dissolved (%) | 98 | 100 | 101 | 99 |

An x-ray powder diffraction test was conducted on this sample and suggests that the doxepin hydrochloride was in an amorphous state.

Various concentrations of alcohol and isopropanol (0-75% w/w in water), as well as different film-forming materials (hydroxypropyl cellulose, ethylene glycol, vinyl alcohol graft copolymer, polyvinyl alcohol, copovidone, polyethylene oxide), were tried, and doxepin hydrochloride in the produced transmucosal film was all in an amorphous state. Those transmucosal films all had uniform appearance and a rapid dissolution profile.

Example 3: Stability of Doxepin Hydrochloride Transmucosal Film (Amorphous State, Without Stabilizer)

In this example, the doxepin hydrochloride transmucosal film was prepared via the method stated in Example 1 and the formulation below. As in Example 2, the doxepin hydrochloride was in an amorphous state in the final film.

| | |
|---|---|
| Doxepin hydrochloride (Crystalline) | 1.0 mg (5.0% w/w) |
| Hydroxypropyl Cellulose | 18.70 mg (93.5% w/w) |
| FD&C Yellow No. 6 | 0.10 mg (0.5% w/w) |
| Sucralose | 0.2 mg (1.0% w/w) |
| Purified Water | 105 mg (Removed during manufacturing process) |

According to the accelerated stability experiment, the undesired related substances (RS A and RS C) of doxepin prepared in this example increased above the acceptance criteria during the accelerated period as shown in Table 3. Thus, the inventors discovered that a stabilizer should be added into the formulation to improve the stability of the composition.

TABLE 3

Accelerated Stability Result (No Stabilizer)

| Accelerated Condition (40° C., 75% RH) | Acceptance Criteria | Example 3 |
|---|---|---|
| 0 day | RS A* ≤ 1.0% | RS A: 0.02% |
| | RS C* ≤ 0.5% | RS C: 0.02% |
| | Total ≤ 2.0% | Total: 0.05% |
| 1 Month | | RS A: 0.55% |
| | | RS C: 0.60% |
| | | Total: 1.33% |
| 3 Month | | RS A: 1.21% |
| | | RSC: 1.50% |
| | | Total: 3.43% |

*Notes:
RS A: USP Doxepin Related Compound A RS, $C_{14}H_{10}O_2$
RS C: USP Doxepin Related Compound C RS, $C_{18}H_{19}NO \cdot HCl$

Example 3: Stability of Doxepin Hydrochloride Transmucosal Film (Amorphous State, Added Some Stabilizers—Not Acceptable)

In this example, different stabilizers such as edetate disodium (EDTA), sodium sulfite, sodium metabisulfite, and sodium Bisulfite were each added as a stabilizer to prepare the doxepin hydrochloride transmucosal film according to Example 1 and the formulation below. As in Example 2, the doxepin hydrochloride was in an amorphous state in the final film.

| | |
|---|---|
| Doxepin hydrochloride | 1.0 mg (5.0% w/w) |
| Hydroxypropyl Cellulose | 18.60 mg (93.0% w/w) |
| Edetate Disodium, or (Sodium Sulfite/Sodium Metabisulfite/Sodium Bisulfite) | 0.10 mg (0.5% w/w) |
| FD&C Yellow No. 6 | 0.10 mg (0.5% w/w) |
| Sucralose | 0.2 mg (1.0% w/w) |
| Purified Water | 105 mg (Removed during manufacturing process) |

According to the accelerated stability experiment, the undesired related substance of the sample prepared in this example still increased significantly during the accelerated period as shown in Table 4.

TABLE 4

Accelerated Stability Result of Different Stabilizers

| Accelerated Condition (40° C., 75% RH) | Acceptance Criteria | Edetate Disodium | Sodium Sulfite | Sodium Metabisulfite | Sodium Bisulfite |
|---|---|---|---|---|---|
| 0 day | RS A* ≤ 1.0% | RS A: 0.02% | RS A: 0.03% | RS A: 0.01% | RS A: 0.05% |
| | RS C* ≤ 0.5% | RS C: 0.02% | RS C: 0.08% | RS C: 0.03% | RS C: 0.12% |
| | Total ≤ 2.0% | Total: 0.05% | Total: 0.16% | Total: 0.05% | Total: 0.19% |
| 1 Month | | RS A: 0.50% | RS A: 0.09% | RS A: 0.12% | RS A: 0.17% |
| | | RS C: 0.61% | RS C: 0.84% | RS C: 0.37% | RS C: 0.92% |
| | | Total: 1.28% | Total: 1.68% | Total: 0.62% | Total: 1.57% |
| 3 Month | | RS A: 1.12% | RS A: 0.24% | RS A: 0.35% | RS A: 0.42% |
| | | RS C: 1.58% | RS C: 2.07% | RS C: 0.93% | RS C: 2.16% |
| | | Total: 2.94% | Total: 3.03% | Total: 1.82% | Total: 2.73% |

Various percentages (0% to 5% w/w) of stabilizers as shown in Table 4 were tested. However, the undesired related substance A or C in the transmucosal film still increased significantly during the accelerated period and exceeded the standard limit.

Example 5: Stability of Doxepin Hydrochloride Transmucosal Film (Amorphous State, Added Selected Stabilizers-Acceptable)

In this example, different stabilizers such as ascorbic acid, butylated hydroxyanisole (BHA), butylated hydroxytoluene (BHT), citric acid, ascorbic acid+BHT, were each added as a stabilizer to prepare the doxepin hydrochloride transmucosal film according to Example 1 and the formulation below.

| | |
|---|---|
| Doxepin hydrochloride | 1.0 mg (5.0% w/w) |
| Hydroxypropyl Cellulose | 18.60 mg (93.0% w/w) |
| Ascorbic Acid, or | 0.10 mg (0.5% w/w) |
| Butylated Hydroxyanisole (BHA), or | |
| Butylated Hydroxytoluene (BHT), or | |
| Citric Acid, or | |
| Ascorbic Acid + BHT | |
| FD&C Yellow No. 6 | 0.10 mg (0.5% w/w) |
| Sucralose | 0.2 mg (1.0% w/w) |
| Purified Water | 105 mg (Removed during manufacturing process) |

According to the accelerated stability experiment, the stability of the sample prepared in this example was good during the accelerated period as shown in Table 5.

TABLE 5

Accelerated Stability Result of Different Stabilizers

| Accelerated Condition (40° C., 75% RH) | Acceptance Criteria | Ascorbic Acid | Butylated Hydroxy anisole (BHA) | Butylated Hydroxytoluene (BHT) | Citric Acid | Ascorbic Acid + Butylated Hydroxytoluene (BHT) |
|---|---|---|---|---|---|---|
| 0 day | RS A* ≤ 1.0% | RS A: 0.02% | RS A: 0.00% | RS A: 0.00% | RS A: 0.02% | RS A: 0.00% |
| | RS C* ≤ 0.5% | RS C: 0.00% | RS C: 0.02% | RS C: 0.01% | RS C: 0.00% | RS C: 0.00% |
| | Total ≤ 2.0% | Total: 0.04% | Total: 0.03% | Total: 0.03% | Total: 0.03% | Total: 0.01% |
| 1 Month | | RS A: 0.08% | RS A: 0.01% | RS A: 0.00% | RS A: 0.04% | RS A: 0.00% |
| | | RS C: 0.02% | RS C: 0.12% | RS C: 0.09% | RS C: 0.02% | RS C: 0.01% |
| | | Total: 0.15% | Total: 0.17% | Total: 0.13% | Total: 0.09% | Total: 0.05% |
| 3 Month | | RS A: 0.32% | RS A: 0.03% | RS A: 0.01% | RS A: 0.16% | RS A: 0.02% |
| | | RS C: 0.04% | RS C: 0.24% | RS C: 0.21% | RS C: 0.03% | RS C: 0.04% |
| | | Total: 0.45% | Total: 0.41% | Total: 0.32% | Total: 0.22% | Total: 0.13% |

Different amounts of ascorbic acid were tested, and the results show that from 0.1% to 2% (w/w) enhanced the stability of the transmucosal film.

Different amounts (0.05% to 5% w/w) of other stabilizers (citric acid, BHA, or BHT), or the combination were tested, and the results show that all of the tested stabilizers enhanced the stability of the transmucosal film.

Example 6: Doxepin Hydrochloride Transmucosal Film (Without an Adhesive)

In this example, the doxepin hydrochloride transmucosal film was prepared via the method stated in Example 1 and the formulation below.

| | |
|---|---|
| Doxepin hydrochloride | 0.10 mg (0.5% w/w) |
| Copovidone | 19.20 mg (96.0% w/w) |
| Ascorbic Acid | 0.40 mg (2.0% w/w) |
| FD&C Yellow No. 6 | 0.10 mg (0.5% w/w) |
| Sucralose | 0.20 mg (1.0% w/w) |
| Purified Water | 105 mg (Removed during manufacturing process) |

According to the adhesion test conducted on beagle dog oral mucosa, the films prepared in this example did not have an acceptable adhesive performance and detached from the mucosa at some point in time. Therefore, the inventors conclude that an adhesive agent should be added to the formulation to promote the adhesion of the transmucosal film to oral mucosa.

Example 7: Doxepin Hydrochloride Transmucosal Film (Adhesive Added)

In this example, the polycarbophil was used as the adhesive agent, and the doxepin hydrochloride transmucosal film was prepared via the method stated in Example 1 and the formulation below.

| | |
|---|---|
| Doxepin hydrochloride | 0.10 mg (0.5% w/w) |
| Copovidone | 19.00 mg (95.0% w/w) |
| Ascorbic Acid | 0.40 mg (2.0% w/w) |
| Polycarbophil | 0.20 mg (1.0% w/w) |
| FD&C Yellow No. 6 | 0.10 mg (0.5% w/w) |
| Sucralose | 0.20 mg (1.0% w/w) |
| Purified Water | 105 mg (Removed during manufacturing process) |

According to the adhesiveness test conducted on beagle dog oral mucosa, the oral films prepared in this example show acceptable adhesive performance that the oral films adhered to the mucosa until completely dissolved.

Different amounts of adhesive agent polycarbophil were tested, and the results show from 1% to 10% (w/w) of polycarbophil enhanced the adhesive performance visibly.

Additionally, other adhesives (carboxymethylcellulose sodium, carbomer, sodium alginate, and povidone) and different amounts (1% to 50% w/w) were tested. The results show that carboxymethylcellulose sodium and sodium alginate did not improve adhesiveness, while carbomer and povidone from 1% to 30% (w/w) enhanced the adhesive performance significantly. However, when the adhesive agents exceed 50% (w/w), the dissolution rate of doxepin was slowed down and not desirable. A proper amount of an adhesive agent is about 1 to 30% (w/w).

Example 8: Doxepin Hydrochloride Transmucosal Film (Single Layer Film)

In this example, the doxepin hydrochloride transmucosal films were manufactured via the method stated in Example 1 and the formulation below.

| | |
|---|---|
| Doxepin hydrochloride | 5 mg (25.00% w/w) |
| Polyvinyl Alcohol | 14.28 mg (71.40% w/w) |
| Butylated Hydroxyanisole | 0.2 mg (1.00% w/w) |
| Polycarbophil | 0.4 mg (2.00% w/w) |
| FD&C Yellow No. 6 | 0.02 mg (0.10% w/w) |
| Sucralose | 0.1 mg (0.50% w/w) |
| 50% Alcohol | 105 mg (Removed during manufacturing process) |

The palatability test of the oral films prepared in this example was conducted on several volunteers. After the oral film was dissolved and the drug was released, the subjects noted that their tongues felt numb, which was caused by the diffusion of doxepin. Therefore, the inventors conclude that a bilayer film should be used to improve the palatability of the transmucosal film.

Example 9: Doxepin Hydrochloride Transmucosal Film (Bilayer Film)

In order to improve the palatability of the composition, the doxepin hydrochloride was prepared as bilayer transmucosal films in this example. The formulation is listed below.

Mucoadhesive Layer

| | |
|---|---|
| Doxepin hydrochloride | 5 mg (25.00% w/w) |
| Polyvinyl Alcohol | 14.28 mg (71.40% w/w) |
| Butylated Hydroxyanisole | 0.2 mg (1.00% w/w) |
| Polycarbophil | 0.4 mg (2.00% w/w) |
| FD&C Yellow No. 6 | 0.02 mg (0.10% w/w) |
| Sucralose | 0.1 mg (0.50% w/w) |
| 50% Alcohol | 105 mg (Removed during manufacturing process) |

Backing Layer

| | |
|---|---|
| Hydroxyethyl Cellulose | 17.60 mg (88.0% w/w) |
| Titanium Dioxide | 2.00 mg (10.0% w/w) |
| Sucralose | 0.20 mg (1.0% w/w) |
| Menthol | 0.20 mg (1.0% w/w) |
| 50% Alcohol | 105 mg (Removed during manufacturing process) |

Preparation:

Mucoadhesive layer: Dissolved the doxepin hydrochloride into the solvent according to the formulation, then added the other components in the formulation and stirred until they were completely dissolved. Set aside or vacuumed to remove air bubbles. Coated the defoamed film solution on the conveyor belt evenly and dried up at the temperature of about 50° C. to 80° C. The aqueous solvent was evaporated after drying. When the film was formed, took the film out for the next process.

Backing layer: Added all components other than the titanium dioxide in the formulation into the solvent. Stirred until they were completely dissolved, then added the titanium dioxide, stirred and dispersed evenly. Set aside or vacuumed to remove air bubbles. Evenly coated the defoamed film solution on top of the previous dried mucoadhesive film on the conveyor belt and dried up at the temperature of about 50° C. to 80° C. The aqueous solvent was evaporated after drying. After the film was formed, cut the film into a suitable size and shape, and immediately wrapped or bagged each piece.

The doxepin hydrochloride transmucosal films prepared in this example provided satisfactory film-forming performance and could be easily peeled off from the film base, and the films had a smooth appearance and uniform color. No visible crystal solid was seen in the transmucosal films. The backing layer had a white color and the mucoadhesive layer had an orange color.

According to the palatability test of the oral films prepared in this example, which was conducted on several volunteers, no feeling of numbness was reported during the entire drug administration process.

In further experiments, other film-forming materials of backing layer, such as ethylene glycol and vinyl alcohol graft copolymer (PVA-PEG), hydroxyethyl cellulose, polyvinyl alcohol, povidone, hypromellose, ethyl cellulose, with various amounts from 80% to 100% w/w, were also tested. The results showed that povidone and PVA-PEG had negligible effects on improving the palatability of the oral film. On the contrary, hydroxyethyl cellulose, polyvinyl alcohol, hypromellose, or ethyl cellulose, or a combination of them, with the amount from 80% to 100% (w/w), significantly improved the palatability of the oral film.

In Example 10-3, sucralose (a sweetener) and menthol (a flavoring agent) were added in the backing layer formulation to improve the taste of the drug composition. The volunteers felt the film tasted better, with a slight sweetness and minty taste, like a sugar film. In further experiments, other sweeteners and flavoring agents for the backing layer, such as aspartame, saccharin sodium, neotame, acesulfame, peppermint oil, orange flavor, pineapple flavor, cherry flavor, blueberry flavor, and grape flavor, with various amounts from 0.01% to 5% w/w, were also tested, and the results show that all of the tested sweeteners and flavoring agents provided a better taste of the transmucosal film.

Example 10: Bioavailability of Doxepin Hydrochloride Transmucosal Films

The doxepin hydrochloride transmucosal films in Examples 10-1 and 10-2 were manufactured via the method stated in Example 1 and the formulation below, while the transmucosal films in Example 10-3 were manufactured via the method stated in Example 9 and the formulation below.

TABLE 6

Components of Different Films

| | | Example | | |
|---|---|---|---|---|
| | | 10-1 | 10-2 | 10-3 |
| | | | Group | |
| | | Single Layer Film | Single Layer Film with Adhesive Agent | Bilayer Film |
| ML[1] | Doxepin Hydrochloride | 3 mg (15.0% w/w) | 3 mg (15.0% w/w) | 3 mg (15.0% w/w) |
| | Polyvinyl Alcohol | 15.68 mg (78.4% w/w) | 15.28 mg (76.4% w/w) | 15.28 mg (76.4% w/w) |
| | BHT | 0.2 mg (1.0% w/w) | 0.2 mg (1.0% w/w) | 0.2 mg (1.0% w/w) |
| | Polycarbophil | — | 0.4 mg (2.0% w/w) | 0.4 mg (2.0% w/w) |
| | FD&C Yellow No 6 | 0.02 mg (0.1% w/w) | 0.02 mg (0.1% w/w) | 0.02 mg (0.1% w/w) |
| | Sucralose | 0.1 mg (0.50% w/w) | 0.1 mg (0.50% w/w) | 0.1 mg (0.50% w/w) |
| | 50% Alcohol | 105 mg (Removed during manufacturing process) | 105 mg (Removed during manufacturing process) | 105 mg (Removed during manufacturing process) |
| BL[2] | Hydroxyethyl Cellulose | — | — | 17.60 mg (88.0% w/w) |
| | Titanium Dioxide | | | 2.00 mg (10.0% w/w) |
| | Sucralose | | | 0.20 mg (1.0% w/w) |
| | Menthol | | | 0.20 mg (1.0% w/w) |
| | 50% Alcohol | | | 105 mg (Removed during manufacturing process) |

[1]ML refers to Mucoadhesive Layer;
[2]BL refers to Backing Layer.

The pharmacokinetic test was conducted on several volunteers. Each group of three volunteers was administered: (i) doxepin hydrochloride transmucosal films manufactured according to Examples 10-1, 10-2 or 10-3, 3 mg dosage; and (ii) doxepin hydrochloride oral tablets, 3 mg dosage. The blood samples were taken before administration (0 min), and 0.5 h, 1 h, 1.5 h, 2 h, 2.5 h, 3 h, 3.5 h, 4 h, 6 h, 8 h, 10 h, 12 h, 24 h, 48 h after administration, respectively. The blood samples were then used to determine the doxepin hydrochloride plasma concentration via the LC-MS/MS method and to calculate the bioavailability of the transmucosal films prepared in the examples. As shown in Table, the bioavailability of the transmucosal films prepared in Examples 10-1, 10-2, and 10-3 are 486%, 625%, and 672% of the oral tablets, respectively. The $T_{max}$ of them are 1.0 h, 0.67 h and 1.0 h, respectively, which is much lower than that of the oral tablets (3.0 h).

The results show that the transmucosal films administered via buccal or sublingual mucosa were absorbed significantly faster than oral tablets, and the bioavailability of the transmucosal films was dramatically higher than that of the oral tablets. In addition, the bioavailability (625%) of transmucosal films with adhesive agent prepared in Example 10-2 was much higher than the bioavailability (486%) of transmucosal films without adhesive agent prepared in Example 10-1. The results show that adding adhesive agent into the formulation improved the bioavailability of the composition significantly. Moreover, the bioavailability of transmucosal films with backing layer in Example 10-3 was 672%, which was higher than that of transmucosal films without backing layer in Example 10-2. The results show that using a bilayer formulation enhanced the bioavailability in addition to improving taste.

TABLE 7

Bioavailability Test of Different Films

| | Pharmacokinetic parameter | | | |
|---|---|---|---|---|
| | Tablets | Example 10-1 | Example 10-2 | Example 10-3 |
| | | | Group | |
| | Reference | Single Layer Film | Single Layer plus Adhesive | Bilayer Film |
| Mean $T_{max}$ (h) | 3.0 | 1.0 | 0.67 | 1.0 |
| Mean $C_{max}$ (ng/ml) | 0.61 | 3.37 | 4.78 | 5.86 |
| Mean $AUC_{0\text{-}48\ h}$ (hr*ng/ml) | 5.93 | 28.85 | 37.08 | 42.95 |
| Relatively bioavailability | — | 486% | 625% | 672% |

The invention, and the manner and process of making and using it, are now described in such full, clear, concise and exact terms as to enable any person skilled in the art to which it pertains to make and use the same. It is to be understood that the foregoing describes preferred embodiments of the present invention, and that modifications can be made therein without departing from the scope of the present invention as set forth in the claims. To particularly point out and distinctly claim the subject matter regarded as invention, the following claims conclude this specification.

What is claimed is:

1. An oral transmucosal doxepin film, comprising:
    (a) a mucoadhesive layer comprising 0.5-25% w/w of doxepin or a pharmaceutical acceptable salt thereof, in an amorphous form, 50-96% w/w of a first film-forming material, 1-30% w/w of an adhesive, and 0.01-10% w/w of a stabilizer, and
    (b) a water-soluble backing layer comprising a second film-forming material to prevent doxepin from diffusing to the oral cavity of a patient during oral administration;
    wherein the first film-forming material is selected from the group consisting of: polyvinyl alcohol (PVA), hypromellose (HPMC), hydroxypropyl cellulose (HPC), copovidone, povidone, ethylene glycol and vinyl alcohol graft copolymer (PVA-PEG), xanthan gum, pectin, polyethylene oxide (PEO), chitosan, and any combination thereof,
    the second film-forming material is selected from the group consisting of: PVA, HPMC, ethyl cellulose, PEO, hydroxyethyl cellulose, and any combination thereof, and
    the stabilizer is selected from the group consisting of ascorbic acid, citric acid, butylated hydroxyanisole (BHA), butylated hydroxytoluene (BHT), and any combination thereof.

2. The film according to claim 1, wherein the first film-forming material is PVA, copovidone, HPMC, HPC, PVA-PEG, PEO, or any combination thereof.

3. The film according to claim 1, wherein the adhesive is selected from the group consisting of polycarbophil, povidone, polyglutamic acid, carbomer, dextran sulfate, and chondroitin sulfate, or any combination thereof.

4. The film according to claim 1, wherein the adhesive is polycarbophil, povidone, or carbomer.

5. The film according to claim 1, wherein the mucoadhesive layer or backing layer further comprises one or more flavoring agents.

6. The film according to claim 1, wherein the flavoring agent is sucralose or menthol.

7. The method for preparing the film of claim 1, comprising the steps of:
    (a) mixing doxepin, the first film-forming material, the adhesive, and the stabilizer in a first aqueous solvent to prepare a mucoadhesive film solution;
    (b) coating the mucoadhesive film solution on a substrate and drying the film solution to form the mucoadhesive layer;
    (c) mixing a second film-forming material in a second aqueous solvent to prepare a backing film solution;
    (d) coating the backing film solution on the mucoadhesive layer and drying the backing film solution to form a bilayer film on the substrate; and
    (e) removing the bilayer film from the substrate to form the oral transmucosal doxepin film.

8. The method of claim 7, wherein the first aqueous solvent comprises 0-75% w/w of an organic solvent selected from the group consisting of: ethanol, isopropanol, acetone, ethyl acetate, tert-butanol, dichloromethane, and any combination thereof.

9. The method of claim 8, wherein the organic solvent is ethanol or isopropanol.

* * * * *